(12) United States Patent  (10) Patent No.: US 6,357,306 B1
Jaeger                      (45) Date of Patent: Mar. 19, 2002

(54) FLUID SAMPLER AND METHOD (76) Inventor: Ben E. Jaeger, 50 Hunter La., Bristol, IL (US) 60512

( * ) Notice: Subject to any disclaimer, the term of this patent is extended or adjusted under 35 U.S.C. 154(b) by 0 days.

(21) Appl. No.: 09/300,644

(22) Filed: Apr. 27, 1999

(51) Int. Cl.$^7$ ................................................. G01N 1/14
(52) U.S. Cl. ................................................. 73/863.83
(58) Field of Search .................... 73/863.81–863.86

(56) References Cited

U.S. PATENT DOCUMENTS

| | | | |
|---|---|---|---|
| 3,747,411 A | * 7/1973 | McDermott et al. | 73/863.85 |
| 4,147,062 A | 4/1979 | Jaeger | |
| 4,262,533 A | 4/1981 | Jaeger | |
| 4,475,410 A | 10/1984 | Jaeger | |
| 4,744,255 A | 5/1988 | Jaeger | |

* cited by examiner

Primary Examiner—Robert Raevis
(74) Attorney, Agent, or Firm—Pyle & Piontek (57) ABSTRACT A sampling apparatus is adapted to obtain samples of fluid product of a type that tends to form a dead layer of product on inner walls of a process line. The apparatus has a sampler body having a bore that opens at a forward end of the body. A plunger in the bore has a sample obtaining recess intermediate its ends. The apparatus is coupled to the process line at an opening to the process line and has two motors. One motor reciprocates the sampler body between a first position where its forward end is retracted to the exterior of a flow stream of product in the process line that exists inwardly of the dead layer of product, and a second position where its forward end extends into the flow stream. The second motor operates, when the sampler body is in the second position, to reciprocate the plunger forward in the bore to project the plunger recess out of the bore and into the flow stream to obtain a sample of fluid product in the recess and then rearward to retract the plunger recess into the bore to a sample delivery point where the sample is removed from the recess and collected. When in the first position, the sampler body is out of the flow stream and does not interfere with or create turbulence in a flow stream or impede passage past the sampler of any scarifying plugs that may be passed through the process line to remove built up product.

26 Claims, 3 Drawing Sheets

FLUID SAMPLER AND METHOD

BACKGROUND OF THE INVENTION

The present invention relates to apparatus for extracting samples of a fluidic product from process lines, pipes or vessels.

Certain manufacturing operations require that the immediate or overall composition of a liquid or fluid product flowing through a process line or contained within a vessel or tank be monitored. Such monitoring ordinarily is accomplished with sampling apparatus, which takes samples of product from a main body of the product Where a composite sample is required, the sampler may be periodically operated to withdraw a series of measured samples of product passing a sampling point. The series of samples are collected and admixed to form a representative sample of the total volume of product Other uses for samplers are in on-line analysis applications, in which the immediate composition of a product must be determined. For this application, the individual samples are not collected as a composite sample, but instead are analyzed separately.

Four exemplary types of prior sampling apparatus are disclosed in U.S. Pat. Nos. 4,147,062, 4,262,533, 4,475,410 and 4,744,255, issued to Ben E. Jaeger, the present inventor and teachings of which are incorporated herein by reference. Sampling apparatus of the type disclosed in said patents is attached to a port to a process line or vessel containing the liquid or fluid product. This enables a product sample obtaining recess in a plunger of the sampler to be extended into the product to receive a product sample in the recess. The plunger is then retracted to deliver the product sample to a collection point in the sampler.

The access line usually is attached to the product-containing process line by an adapter connected and sealed to the process line around an opening therein. The sampler may include, as described in said Jaeger patents, a sampler body having a bore in which a plunger having a sample obtaining recess is reciprocated. The bore communicates with the process line interior through the adapter and process line opening. The plunger is reciprocated to a sample obtaining position in which the plunger recess is extended out of the body bore and into the process line to receive a sample of the product therein. The plunger is then reciprocated to a sample delivering position in which the plunger recess is retracted into the bore to deliver the sample to a point in the bore where the sample is removed from the recess and collected.

The interior of the vessel or process line is a pressure boundary of the vessel, pipe or process line and the exterior is outside of the pressure boundary. The process line defines within its inner walls a flow path for the product. The product does not necessarily flow through the entire cross-sectional area of the flow path, so a flow stream of the product, which is the normal continuous flow path of the fluid product through the process line, is within and of the same or a smaller cross-sectional area than the flow path. The sampler adapter that communicates with the opening to the process line may comprise a recessed tee or pullout, the recessed portion of which is part of and within the interior of the process line and therefore within the pressure boundary.

The fluid product flows through the process line in the flow stream. The product may be a liquid or a fluidized solid that is highly viscous, stringy, gummy or abrasive, and its solids content may be a soft granular material that is generally gummy, a stringy fibrous material such as paper pulp, or a hard and abrasive material such as sand. Depending upon the nature of the product, it can build up on, deposit on, or stagnate adjacent to and along the inner walls of the process line. This results in a dead layer of the product on and along the process line inner walls and in the cross-sectional area of the flow stream often being smaller than the cross-sectional area of the flow path through the process line. The flow stream then exists inwardly from the inner walls of the process line and the dead layer of product. A deposited layer of the solids component of the product on the process line inner walls can be caused by density differences between the solids and the liquid components of the product, which can result in stratification of the product and settling out of solids along the product flow path through the process line. Should the product comprise a stringy fibrous material such a paper pulp, a layer of the solids component can build up on the process line inner walls as a result of dewatering of the solids component as the flow rate of the product, adjacent to the walls, slows relative to the flow rate toward the center of the flow stream. Also, a boundary layer of relatively stagnant product can occur if the product is highly viscous but otherwise homogeneous and clean. A highly viscous product exhibits a flow distribution curve that is characterized by the product having that a velocity that approaches zero at the inner walls of the process line and increases to a maximum at the center of the flow stream.

With fluid products that deposit and build up in a layer on inner walls of process lines, the thickness of the layer can increase and move inward, resulting in a progressive decrease in the cross-sectional area of the product flow stream. This, in turn, can result in a progressive decrease in the flow rate of product through the process line which, if allowed to continue, could result in significant blockage of the line. With such products, from time to time it often is necessary to pass scarifying plugs through the process lines to clean built up of material from the walls of the lines.

Samplers of the types disclosed in the aforementioned Jaeger patents may be used to sample fluid products that tend to deposit and build up or otherwise form a dead layer of product on inner walls of process lines. Because it may be necessary from time to time to pass scarifying plugs through a process line to remove built up of product, such a sampler must be coupled to the line so that its forward end does not normally protrude into the interior of the line. This is necessary to prevent the sampler forward end from blocking passage of any scarifying plugs. However, as product builds up in the process line and moves radially inward from the sampler forward end, the sampler and its plunger gradually and effectively become spaced further and further from the flow stream of product that exists toward the center of the line inwardly of the dead layer of product. This is not a desirable situation, since during a sampling operation the forward end of the sampler may be sufficiently far away from the flow stream that the sample obtaining recess in the plunger cannot be projected fully past the built up thickness of product into the flow stream. The result is that the product sample obtained may not be a valid representation of the product in the flow stream. Also, even if the plunger recess can be projected fully into the flow stream, upon retraction it will pass through the dead layer of product, which can result in contamination of the sample.

Even if the product sampled is not of the type that builds up on and must be removed from inner walls of a process line by scarifying plugs, the samplers of the aforementioned Jaeger types may not necessarily obtain product samples that are valid representations of the product in the flow stream.

This can occur, for example, if the fluid product is highly viscous, such that its flow component toward the inner walls of the line is slower than toward the center of the flow stream. In this case, unless the sample delivering recess in the plunger can be projected beyond the dead layer comprising the stagnant slow or no flow rate portion of the flow stream, a valid product sample may not be obtained. Nor can this problem be properly overcome by mounting the sampler so that its forward end is always within the flow stream in the process line, since this could, and often would, undesirably decrease the cross-sectional flow area of and create turbulence in the flow stream.

OBJECT OF THE INVENTION

An object of the present invention is to provide a fluid sampler of the reciprocating plunger type, that is adapted to be coupled to and obtain valid product samples from a process line in which there is a flow of a product that tends to build up on, deposit on or stagnate along inner walls surfaces of the process line in a dead layer of product Another object is to provide such a sampler, a body portion of which has a forward end that can selectively be positioned either to the exterior or to the interior of a flow stream of product through the process line.

Yet another object is to provide such a sampler, the forward end of the body of which can be positioned at selected locations within the interior of the process line.

A further object of the invention is to provide such a sampler in which the forward end of the sampler body may be positioned within the process line inward from a dead layer of product on inner walls of the process line during a sampling operation, to obtain a valid product sample from a flow stream of the product toward an axial center of the process line and without contamination of the sample by product from the dead layer.

SUMMARY OF THE INVENTION

In accordance with the present invention, a fluid sampling apparatus is operable to obtain discrete samples of fluid product from a process line. The sampling apparatus includes a sampler body having a bore with a forward opening at a forward end of the sampler body. A plunger in the sampler body bore has a fluid product sample-receiver, and an adapter connects the sampling apparatus to the process line at an opening to the process line. A motor reciprocates the sampler body between a first position where the forward end of the sampler body is retracted to the exterior of a product flow stream through the process line and a second position where the forward end is extended into the interior of the flow stream. The motor also reciprocates the plunger in the bore between a sample obtaining position where the plunger sample receiver is extended out of the forward bore opening into the flow stream to obtain in the sample receiver a sample of product, and a sample delivering position where the sample receiver is retracted from the flow stream to a position within the bore where the product sample is collected.

The motor reciprocates the plunger between the sample obtaining and sample delivering positions when the sampler body has been reciprocated to the second position where the forward end of the body extends into the product flow stream. The sample receiver may be an annular recess in and circumferentially around the plunger, and seals on the plunger maintain a fluid seal between the sampler body bore forward opening and the sample delivering position during reciprocation of the plunger.

In the disclosed embodiment, the motor includes first and second motors. The first motor reciprocates the sampler body to move the sampler body forward end between its first position to the exterior and its second position to the interior of the flow stream. The second motor reciprocates the plunger to move the plunger aperture between the sample obtaining and sample delivering positions. The first and second motors may comprise pneumatic motors, the second motor is coupled to the sampler body and to the plunger and the first motor is coupled to the second motor. The second motor reciprocates the plunger relative to the sampler body and process line, and the first motor reciprocates the second motor, the plunger and the sampler body relative to the process line. The second motor has a piston in a cylinder, the cylinder is attached to the sampler body and the piston is attached to a rearward end of the plunger to reciprocate the plunger relative to the sampler body and between the sample obtaining and delivering positions. The first motor has a cylinder, a piston in the cylinder and a piston rod attached at its rearward end to a forward end of the piston and at its forward end to the cylinder of the second motor to reciprocate the second motor, the plunger assembly and the sampler body. The first motor is rearward of the second motor and the piston rod of the first motor and the plunger are axially aligned.

The sampling apparatus is adapted to obtain samples of a fluid product of a type that tends to build up, deposit or stagnate on and along inner walls of the process line in a dead layer of product The adapter connects the sampler body to the process line in sealed relation to the process line opening for reciprocation of the sampler body, by the first motor, forward from the first position to the second position within the product flow stream inwardly of the dead layer of product, and then rearward from the second to the first position to the exterior of the flow stream. With the sampler body in the second position, reciprocation of the plunger by the second motor to the sample obtaining position places the plunger recess inwardly of the dead layer of product and into the product flow stream in the process line for collection of a product sample. With the sampler body in the first position, it is out of the flow stream and main flow path through the process line and does not interfere with movement through the process line of the product flow or of any scarifying plugs that from time to time may be passed through the process line to clean any built up layer of product from the process line inner walls.

The invention also contemplates a method of sampling a fluid product conveyed through a process line. The method comprises the steps providing a sampler body having a bore and a forward opening from the bore at a forward end of the sampler body; positioning a plunger, having a sample receiver intermediate forward and rearward ends thereof, within the bore, and moving the sampler body to move its forward end between a first position to the exterior of a product flow stream through the process line and a second position within the interior of the flow stream. Also included is the step, while the sampler body forward end is at the second position, of reciprocating the plunger to extend the plunger forward through the sampler body bore to a sample obtaining position where the forward end of the plunger and the sample receiver are projected out of the forward bore opening and into the fluid product within the process line to receive in the sample receiver a sample of the product, and to then retract the plunger rearward through the sampler body bore opening and into the bore to deliver the plunger sample receiver and product sample therein to a sample delivering position in the bore. Further included are the steps of removing the sample from the recess at the sample delivering position and periodically repeating the plunger reciprocating and sampler body moving steps.

The method is advantageous for use in obtaining samples of a fluid product of a type that builds up, deposits or stagnates on and along, inner walls of the process line in a dead layer of product, and the step of moving the sampler body forward end to the second position extends the forward end into the process line inwardly beyond the dead layer of product and into the flow stream. This enables collection of a product sample that is generally free of contamination by product from the built up, deposited or stagnated dead layer. Then, when the sampler body is retracted to the first position, it is moved out of the flow stream so as not to interfere with the flow of product or movement of any scarifying plugs that may be passed through the process line.

The foregoing and other objects, advantages and features of the invention will become apparent upon a consideration of the following detailed description, when taken in conjunction with the accompanying drawings.

DETAILED DESCRIPTION

The invention comprises a fluid product sampling apparatus having a sampling plunger that is reciprocated within a sampler body bore between a fluid sample obtaining position and a sample delivering position. The sampling apparatus is adapted to be attached to a process line, pipe or vessel containing a fluid product to be sampled. When so attached, the plunger is reciprocated forward and extended through an open forward end of the bore to position a sample receiver in the plunger, which in the described embodiment comprises a sample obtaining aperture or recess in the plunger, at a sample obtaining position within the fluid product in the process line to receive a sample of product in the recess. The plunger is then reciprocated rearward and retracted back into the bore to move the recess and deliver the fluid sample therein to a sample delivering position within the sampler bore. The sampler is particularly useful for sampling a fluid product of a type that has a tendency to build up, deposit or stagnate on and along inner walls of the process line in a dead layer of product The fluid product flows through the process line, the interior of which is the pressure boundary of the process line and the exterior of which is outside of the pressure boundary. The process line defines within its inner walls a flow path for the product. The product does not necessarily flow through the entire cross-sectional area of the flow path, so a flow stream of the product, which is the normal continuous flow path of the fluid product through the process line, exists within and is of the same or a smaller cross-sectional area than the flow path. An opening to the process line may comprise a recessed tee or pullout, the recessed portion of which is part of and within the interior or the pressure boundary of the process line.

The fluid product flows through the process line in the flow stream. The product may be a liquid or a fluidized solid, it may be highly viscous, stringy, gummy or abrasive, and its solids content may be a soft granular material that is generally gummy, a stringy fibrous material such as paper pulp, or a hard and abrasive material such as sand. Depending upon the nature of the product, it can build up, deposit or stagnate adjacent to and along the inner walls of the process line in a dead layer of product. This results in the cross-sectional area of the flow stream often being smaller than the cross-sectional area of the flow path through the process line. The flow stream then exists a distance inwardly from the inner walls of the process line, i.e., inward from the dead layer of product. A layer of the solids component of the product can deposit on the process line inner walls as a result of density differences between the solids and the liquid components of the product, which can result in stratification of the product and settling out of solids along the product flow path through the process line. Should the product comprise a stringy fibrous material such a paper pulp, a layer of the solids component can build up on the process line inner walls as a result of dewatering of the solids component of the fluid product as the flow rate of the product, adjacent to the walls, slows relative to the flow rate toward the center of the flow stream. Also, a boundary layer of relatively stagnant product can occur adjacent to the process line inner walls if the product is highly viscous but otherwise homogeneous and clean. This happens because a highly viscous product exhibits a flow distribution curve that is characterized by the product having a velocity that approaches zero at the inner walls of the process line and increases to a maximum at the center of the flow stream.

The sampler of the invention is well adapted for use with products of the above described type, both in obtaining uncontaminated or valid samples of fluid product and in obtaining product samples from selected locations in the cross-flow direction within the process line.

According to the invention, the sampler body is carried by and reciprocable relative to a frame that is fixed against movement with respect to the process line. The arrangement enables the forward end of the sampler body, and therefore the forward end of the bore, to be moved to any selected location between a first position outwardly from and a second position within the product flow stream in the process line interior. When moved to the first position, the forward end of the sampler body advantageously, but not necessarily, is retracted sufficiently out of the flow path through the process line so that it can then neither impede nor cause turbulence in the product flow stream, nor can it block passage of any scarifying plugs that may from time to time be passed through the process line to remove a dead layer of product from inner walls of the process line. When moved to the second position, the forward end of the sampler body can selectively be located in or extended through any dead layer of product on the process line inner walls, although to obtain a valid product sample, the forward end would be moved to the interior of the product flow stream. The plunger, when extended from the bore, can therefore have its sample obtaining recess be selectively located at any desired position within the process line in the cross-flow direction, although to obtain a valid sample it would be located within the interior of the flow stream. As a result, the product sample obtained can be selectively taken from the flow stream and/or from the dead layer of product Referring to the drawings, the sampling apparatus is indicated generally at 20 and includes a plunger having sample receiver, which advantageously may comprise an annular recess, that is extended into a process line, pipe or vessel 22 for obtaining in the recess a sample of fluid product from the process line. The plunger is then retracted from the process line to deliver the fluid sample in the recess to a sample delivery point. The recess is sized to obtain and contain a precise volume of the fluid product and the sampler may be periodically actuated so that the fluid samples collected at the delivery point represent a composite sample of the fluid in the process line. The plunger can be reciprocated by any suitable motor means, such as by a pneumatic motor means indicated generally at 24, which as will be described comprises two motor means. Seals on the plunger maintain a fluid seal between the interior of the pressure boundary in the process line and the sample delivery point point, and between the sample delivery point and the motor means, during reciprocation of the plunger. In this manner, the samples are generally insensitive to the pressure of the fluid in the process line and the collected samples are protected against contamination.

More specifically, the sampler 20 has a body 26 with a longitudinal bore 28. A process line adapter 30 couples the sampler with fluid product in the interior of the process line 22, which in the drawings is shown as a pipe. The adapter has a passage 32 and at its forward end connects and is sealed to the process line around a process line opening 34 that provides communication with an interior 36 of the process line and the fluid product therein. The adapter is attached to the process line by a weld 38, and between the forward end of the passage 36 and the pipe opening the adapter defines a recess 39 within which the pressure boundary also exists.

The sampler body 26 has an elongate cylindrical forward end 40 and an elongate cylindrical rearward end 42 of increased diameter. A bushing carrier 44 is around the sampler body cylindrical forward end 40. The bushing carrier has a central passage 46 within which is carried a bushing 48 and a seal 50. The bushing supports the forward end 40 of the sampler body 26 for sliding movement within the bushing carrier and the seal provides a fluid seal between the bushing carrier and sampler body. At its rearward end the bushing carrier has a radial flange 52. The bushing carrier is attached to the adapter by a plurality of fasteners 54 extending through the flange into the adapter. When so attached, a forward cylindrical end 56 of the bushing carrier is received in the adapter passage 32 with a seal 58 providing a fluid seal between the bushing carrier and adapter.

The motor means 24 for operating the apparatus 20 comprises a sampler plunger reciprocating motor means and a sampler body positioning motor means and, respectively indicated generally at 60 and 62. In the described embodiment, each motor means 60 and 62 is a pneumatic motor means, although other types of motor means could be used, such as electric or hydraulic motor means, depending upon the environment of the sampler. The motor means 60 comprises a cylinder 64, a forward end of which is attached to a rearward end of the sampler body 26 by a head 66. The attachment is made by fasteners 68 extending between the rearward portion 42 of the sampler body and the head and by fasteners 70 extending between the head and the forward end of the cylinder 64. A piston 72, carrying an annular seal 74 around its circumference, is slidable in a passage 76 in the cylinder.

A plunger assembly, indicated generally at 78, extends through the sampler body bore 28, through a bore 80 in the head 66 and into the cylinder 64 of the plunger reciprocating motor means 60. The plunger assembly includes a plunger 82 in which is an annular sample receiver, recess, aperture or chamber 84 of predetermined volume. A pair of annular seals 86 is on the plunger forward of the sample obtaining recess and a pair of annular seals 88 is on the plunger rearward of the recess. Wrench flats 90 are on the plunger rearward of the seals 88, from which the plunger extends rearward through a pair of annular seals 92 in the head bore 80 into the cylinder 64 of the motor means 60. At its rearward end, the plunger is attached to the motor means piston 72 by a fastener 94. A cylindrical boss 96 on a forward side of the piston is closely received in a cylindrical recess 98 in a rearward end of the plunger to maintain axial alignment of the piston and plunger.

The sampler positioning motor means 62 comprises a cylinder 100, a forward end of which is attached to a rearward end of a head 102 by fasteners 104. A forward end of the head is attached to rearward ends of a plurality of tie rods 106 by fasteners 108. Forward ends of the tie rods are attached to a rearward end of the bushing carrier 44 by fasteners 110. In the embodiment shown, the tie rods number four and maintain the sampler positioning motor means 62 in rigid spaced relationship to the bushing carrier 44.

The sampler positioning motor means 62 also includes a piston 112 that has an annular seal 114 around its circumference and is received for reciprocation in the cylinder 100. A piston rod 116 extends forwardly from the piston through a bore 118 in the head 102, within which bore are a fluid seal 119 and a bushing 120. A forward end of the piston rod is connected to a rearward end of the cylinder 64 of the motor means 24, and just rearward of its forward end the piston rod is provided with wrench flats 121. The wrench flats accommodate connection of the piston rod to the cylinder 64 by allowing a threaded rod 122 at the front end of the piston rod to be threaded into a tapped blind hole in the rearward end of the cylinder and an enlarged annular rib 124 toward the front of the piston rod to simultaneously be torqued into a countersink 126 in the rearward end of the cylinder. An anti-rotation block 128, attached to the cylinder 64 by fasteners 129, slides along and between a pair of the tie rods 106 to prevent rotation of the cylinders 64 and 100 during operation of the sampling apparatus 20. Prevention of such rotation is necessary to prevent damage to flexible lines that in operation of the sample are normally attached to one or more of the ports 130, 132, 134, 136, 138, 140, 142, 144 and 146.

The arrangement mounts the sampler positioning motor means 62 on a rigid framework comprising the tie rods 106, the bushing carrier 44 and the adapter 30. The arrangement also supports the motor means 60 axially between forward and rearward bushings, i.e., between the bushing 48 of the bushing carrier 44 and the bushing 120 of the head 102, by virtue of the piston rod 116 being countersunk into the rearward end of the cylinder 64.

The piston 72 of the plunger reciprocating motor means 60 urges the plunger assembly 78 forward by introduction of air under pressure at an air inlet 130 in the cylinder 64 and urges the plunger assembly rearward by introduction of air under pressure at an air inlet 132 in the head 66. In turn, the piston 112 of the sampler positioning motor means 62 urges the piston rod 116 forward by introduction of air under pressure at an air inlet 134 in the cylinder 100 and urges the piston rod rearward by introduction of air under pressure at an air inlet 136 in the head 102. A fluid sample discharge or outlet port 138 and an expelling fluid inlet port 140 are diametrically opposed in the rearward end 42 of the sampler body 26 at the sample delivery position within the sampler body bore 28. Diametrically opposed ports 142 and 144 are in the sampler body rearward of the ports 138 and 140, and a port 146 is in the head 66 in communication with the head bore 80.

The plunger assembly 78 is of a slightly smaller diameter than the diameters of the bores 28 and 80 within which it reciprocates. In consequence, the seals 86 and 88 carried by the plunger assembly, and the seals 92 within the head 66, along with the seal 74 on the piston 72, control the concentricity of the plunger assembly within the bores and function as bearings to enable the plunger assembly to reciprocate easily. This prevents direct sliding contact between the relatively hard components of the sampler, whereby the life of the sampler is extended and its repair frequency reduced. The seals 86 and 88 also maintain a fluid seal between the inlet and outlet ports 140 and 138 and the fluid in the process line 22. In addition, the seals wipe the bore 28 clean of sampled fluid with reciprocation of the plunger assembly.

The sampling apparatus 20 is particularly adapted to obtain samples of fluid product of the aforementioned types, which tend to build up, deposit or stagnate on and along inner walls 148 of the process line 22 in a dead layer of product. With such fluid products, the flow stream of the product is of smaller cross-sectional area than the flow path through the process line. This is because the dead layer of product along the process line inner walls effectively reduces the cross-sectional area within the flow path that is available for the flow stream. In other words, the dead layer of product effectively moves the product flow stream radially inward away from the inner process line walls and toward the axial center of the process line. It is normally not desirable to obtain product samples from the dead layer of built up, deposited or stagnant product, since that product is contaminated, at least to the extent that it does not accurately represent the composition of the product in the flow stream. It therefore usually is desirable to be able to obtain product samples from the flow stream radially inward from the dead layer of product along the inner walls of the process line, and that is uniquely accomplished by the sampler of the invention.

To this end, the sampling apparatus is uniquely configured to extend a forward end 152 of the sampler body 26 and a forward opening 154 of the sampler body bore 28 into the process line 22 to a selected location inward from a dead layer of product on the process line inner walls 148 and within the interior of the flow stream to enable an uncontaminated sample of product to be obtained from the flow stream. However, if so desired, the forward end of the sampler body can also be extended so as to be located within the dead layer of product.

Figure 1:
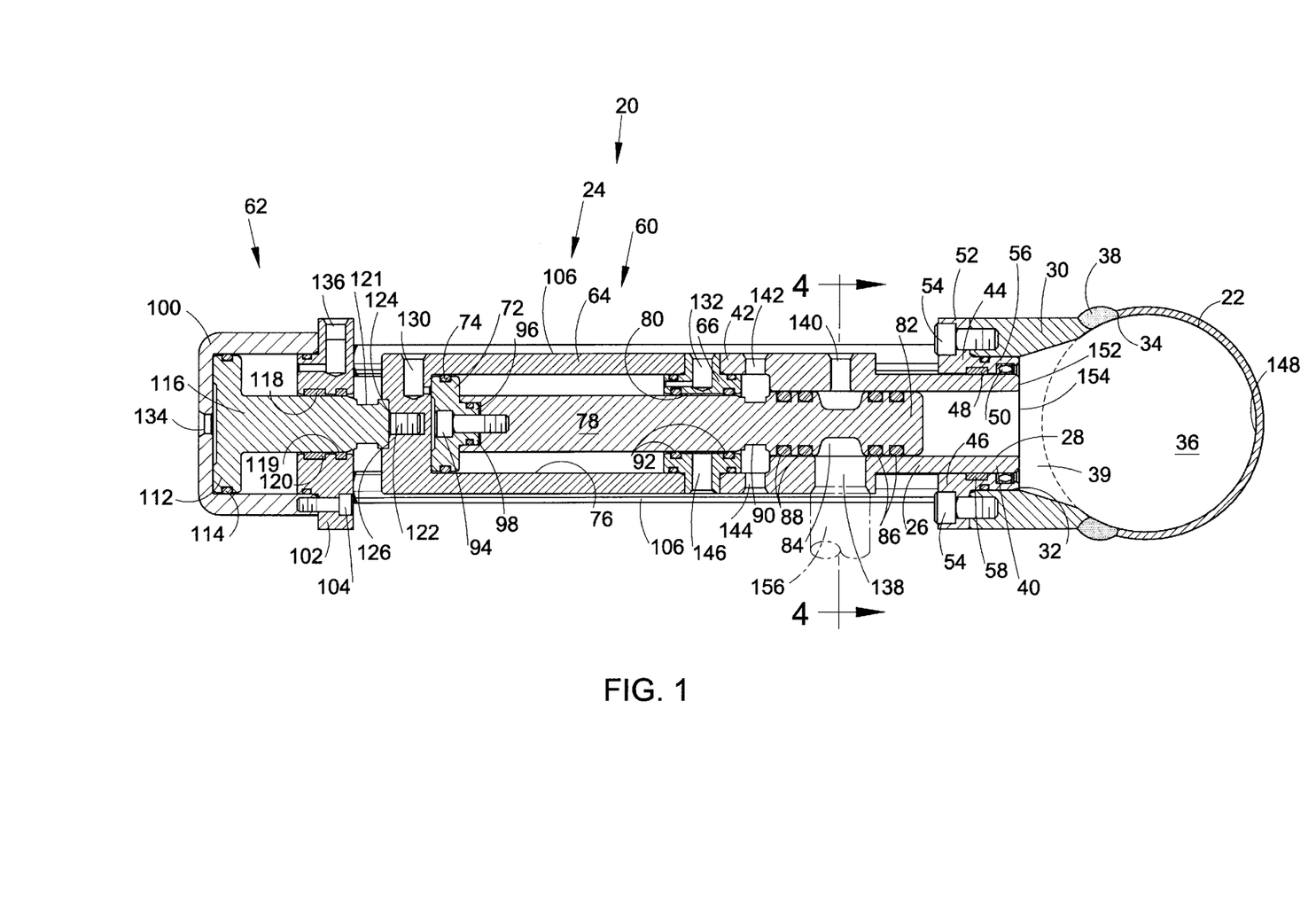
FIG. 1 is a cross-sectional side elevation view of a sampler embodying the teachings of the invention, showing the sampler in its idle position.
Figure 2:
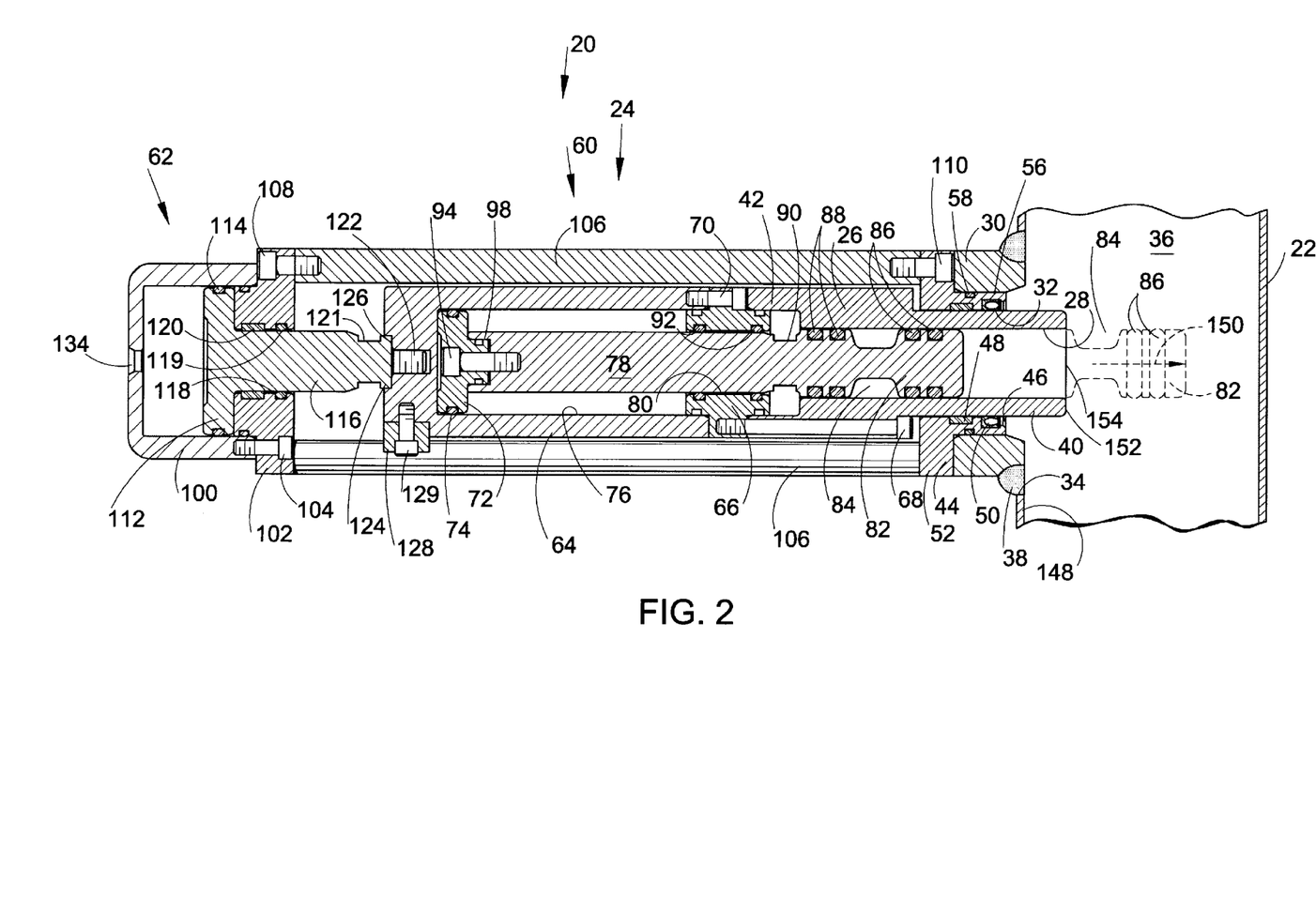
FIG. 2 is a cross-sectional top plan view of the sampler, showing the sampler in each of its sample obtaining and sample delivering positions.
Figure 3:
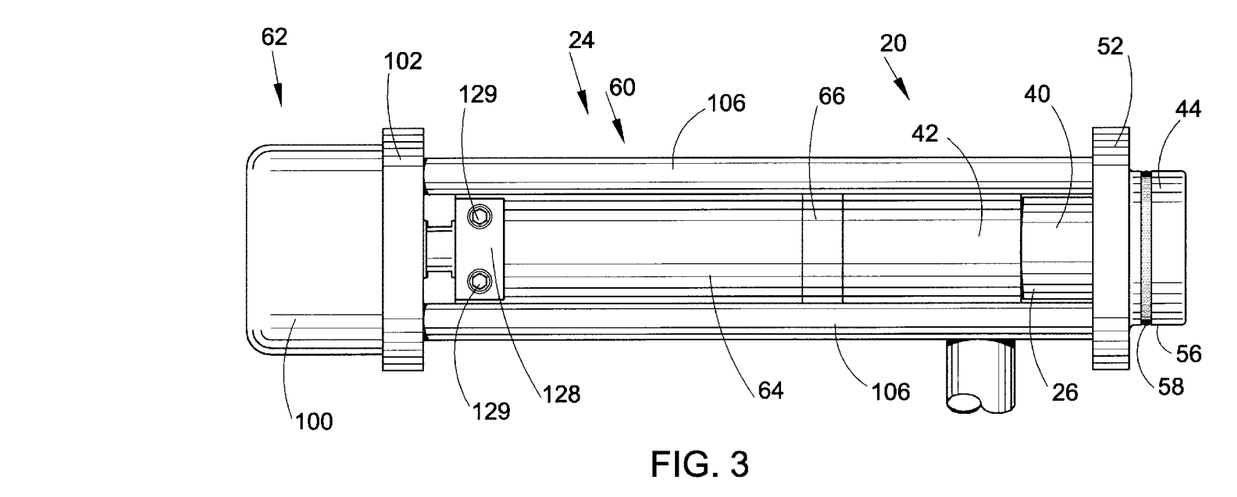
FIG. 3 is a pictorial side elevation view of the sampler.
Figure 4:
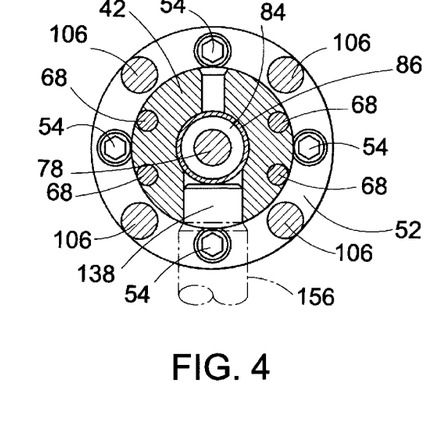
FIG. 4 is a side elevation view, partly in cross-section, taken substantially along the lines 4—4 of FIG. 1.

As shown in FIG. 1, the motor means 24 includes the first motor means or sampler positioning motor means 62. One function of the first motor means is to retract the sampler body forward end 152 to a first position where it is fully out of the product flow stream and preferably out of a main flow path through the process line interior, as shown in FIG. 1. In the first position, the forward end of the sampler body, and therefore the forward opening 154 from the sampler body bore 28, may be positioned at the forward end of the passage 46 through the bushing carrier 44. Another function of the first motor means is to extend or project the sampler body forward end a selected distance forward to a second position, as shown in FIG. 2. In the second position, the forward end of the sampler body may be located at any selected position in the process line in the cross-flow direction, although to obtain valid product samples it would be located within the interior of the product flow stream.

The first position of the sampler body 26 locates the forward end of the sampler body out of the product flow stream through the process line, and preferably out of the main flow path through the process line, as shown in FIG. 1. It therefore cannot block and reduce the flow area of, or introduce undesirable turbulence into, the flow stream. Also, in the first position the sampling apparatus itself is protected against damage by the fluid product. For example, should the fluid product be abrasive, in the first position the forward end of the sampler is isolated from abrasion and damage by the product.

The sampler positioning or first motor means 62 includes the piston 112 and piston rod 116, the forward end of which is attached to the rearward end of the cylinder 64 of the motor means 60. Beginning with the sampling apparatus 20 in its first position as shown in FIG. 1, where the forward end 152 of the sampler body 26 is to the exterior of the flow stream through the process line 22, to obtain one or more samples of fluid product, the first motor means is energized by introducing air under pressure at the air inlet 134 to urge the piston 112 and piston rod 116 rightward or forward to move the sampling apparatus forward from the first position to the second or sampling position. Forward movement of the piston and piston rod push the second motor means cylinder 64, and therefore the plunger assembly 78 and sampler body 26, forward, with the sampler body moving through a front bearing consisting of the bushing carrier 44 and its bushing 48. The length of the stroke of the first motor means 62 is controlled to move the forward end 152 of the sampler body 26 a selected distance into the interior of the process line to a desired sampling location. The selected distance can be more or less than sufficient to move the sampler body forward end inward from and beyond any dead layer of product on the process line inner walls 148, as shown in FIG. 2, but is limited to be less than sufficient to move a product sample delivering line 156 against the rearward side of the bushing carrier 44. This places the sampler in its second or sampling position, in which position the sampler remains while sampling of product occurs. During sampling, the motor means 62 can remain energized, by the continued application of air under pressure at the air inlet 134, to resist rearward movement of the sampler under the urging of the pressure of product acting on the forward ends of the sampler body and plunger assembly 78.

With the sampler body 26 moved to its second position, the second motor means 60 is energized to reciprocate the plunger assembly 78 to obtain samples of fluid product from the process line 22. To collect one or more product samples, pressurized air is introduced to the air inlet 130. This drives the piston 74 and plunger assembly 78 rightward or forward to move the plunger annular sample obtaining recess 84 through the sampler body bore 28 and the forward bore opening 154 into the interior 36 of the process line interior, with the forward end of the plunger then being positioned as indicated by the head of an arrow 150. As the plunger assembly moves forward to extend the recess into the process line, the plunger seals 88 move from behind the ports 138 and 140 to adjacent the front of the sampler body bore. In this manner, the sampler body bore is wiped clean by the seals of any accumulated fluid product with each reciprocation of the plunger assembly. Also, as the plunger assembly is extended, the rearward plunger seals 88 form a fluid seal with the sampler body bore 28 forward from the inlet and outlet ports 140 and 138 before the forward plunger seals 86 move out of the bore. Similarly, upon leftward movement and retraction of the plunger assembly, the seals 86 enter the bore before the seals 88 move over and expose the ports. In consequence, a fluid seal is at all times maintained between the fluid product in the process line 22 and the inlet and outlet ports, and only the fluid sample obtained in the recess 84 ever reaches the sample delivery point at the ports.

Upon extending the plunger assembly 78 forward to obtain a sample of fluid product, if the sample recess 84 is located to the interior of and exposed to the flow stream of product, it will be washed by the flow stream. This cleans any old or contaminated product from the recess, with its annular shape and direct exposure to the flow stream helping to prevent it from becoming clogged by solids. The sample delivering recess is therefore generally self-cleaning of debris that may be encountered in product lines, so that when it is withdrawn into the sampler bore 28, it will carry a valid sample of the fluid product Upon the plunger assembly being fully retracted, the annular recess or sample chamber 84 is positioned at the sample delivery point at the outlet port 138. The product sample in the recess then passes through the sample delivering port and any discharge line 156 that may be connected to the port for immediate analysis or collection, for example by being discharged into a sample collection container (not shown). To facilitate removal of the sample from the plunger recess, if desired a stream of air or other product sample compatible fluid can be introduced through the inlet port 140 to flush or blow the product sample from the recess. Alternatively, vacuum can be applied to the discharge port. The particular expelling fluid applied at the inlet port depends on the nature of the product sampled. Should the product sample require dilution for subsequent analysis, the expelling fluid may comprise the necessary diluent When sampling is over, the forward end of the sampling apparatus 20 is retracted from the second position in the process line 22 to the first position to the exterior of the flow stream and advantageously outside the main flow path through the process line, as shown in FIG. 1. This is accomplished by first applying air under pressure to the air inlet 132 to the second motor means 60 to move the plunger assembly 78 to its retracted position within the bore 28 of the sampler body 26. Next, air under pressure is removed from the air inlet 134, and air under pressure is applied to the air inlet 136, to the first motor means 62. Application of pressurized air to the air inlet 136 urges the piston 112 leftward or rearward to pull the cylinder 64 of the motor means 60, and thereby the sampler body and piston assembly 78, leftward or rearward from the second position to the first position. With the forward end of the sampler body moved to the first position, the sampler cannot impede or create turbulence in the product flow stream. Also, if the first position is outside the main flow path through the process line, scarifying plugs can be passed through the process line without being blocked by the sampler body.

The ports 142 and 144 provide specific advantages in monitoring the need for maintenance of the sampler. With the port 142 closed and the port 144 open, product dripping out of the port 144 visually indicates a need to replace the plunger seals 86 and/or 88. If desired, a sensor can be placed in the port 144 to sense any leakage of product and signal the need to replace the plunger seals. Use of a sensor is particularly advantageous if leakage of product from the sampler were highly undesirable and must be detected right away, such as where the product contains an insecticide or is radioactive. Alternatively, fluid may periodically be introduced at the port 142 to remove any product from around the plunger between the ports 142 and 144 and carry it to a sensor in the port 144 for detection.

The port 146 also serves the purpose of monitoring sampler seal integrity by providing a means to visually check the integrity of the seals 92 to its opposite sides. If the fluid used to operate the second motor means 60 comes out of the port, that is an indication that the rearward seal 92 is worm Should product exit the port, that indicates that the forward seal 92 requires replacement Leakage of product out of the port 146 can also indicate that the port 144 is plugged and/or is not being properly monitored.

While one embodiment of the invention has been described in detail, various modifications and other embodiments thereof can be devised by one skilled in the art without departing from the spirit and scope of the invention, as defined in the accompanying claims.

What is claimed is:

1. Sampling apparatus, comprising:
   a fluid sampler operable to obtain discrete samples of fluid product, said fluid sampler including a sampler body having a bore with a forward opening from said bore at a forward end of said sampler body;
   plunger means in said sampler body bore, said plunger means having a fluid sample receiver therein;
   means for coupling said sampling apparatus to a process line containing a fluid product flow stream, in communication with an opening to the process line, and
   motor means for reciprocating said sampler body between a first position where said forward end of said sampler body is to the exterior of the flow stream and a second position where said forward end of said body is extended into the interior of the flow stream, and for reciprocating said plunger means in said bore between a sample obtaining position where said plunger means sample receiver is extended out of said forward bore opening and into the interior of the flow stream for obtaining in said sample receiver a sample of fluid product and a sample delivering position where said plunger means sample receiver is retracted to the exterior of the flow stream to a sample delivery position within said bore for delivering the sample of fluid product from said sample receiver.

2. Sampling apparatus as in claim 1, wherein said motor means reciprocates said sampler body to said second position before said motor means reciprocates said plunger means to move said plunger means sample receiver between said sample obtaining and said sample delivering positions.

3. Sampling apparatus as in claim 1, wherein said plunger means sample receiver comprises an annular recess in and circumferentially around said plunger means, and including seal means for maintaining a seal between said bore forward opening and said sample delivering position in said bore during reciprocation of said plunger means.

4. Sampling apparatus as in claim 1, wherein said motor means includes first and second motor means.

5. Sampling apparatus as in claim 4, wherein said first motor means reciprocates said sampler body to move said sampler body forward end between its first position to the exterior and its second position to the interior of the flow stream, and said second motor means reciprocates said plunger means to move said plunger means aperture between said sample obtaining and sample delivering positions.

6. Sampling apparatus as in claim 4, wherein said first and second motor means comprise pneumatic motor means.

7. Sampling apparatus as in claim 4, wherein said first motor means is coupled to said second motor means and said second motor means is coupled to said sampler body and said plunger means.

8. Sampling apparatus as in claim 7, wherein said first motor means reciprocates all of said second motor means, said plunger means and said sampler body relative to the process line and said second motor means reciprocates said plunger means, but not said sampler body, relative to the process line.

9. Sampling apparatus as in claim 4, wherein said second motor means comprises pneumatic motor means including a piston in a cylinder and is attached to said sampler body and to a rearward end of said plunger means to reciprocate said plunger means, relative to said sampler body, between said sample obtaining and delivering positions.

10. Sampling apparatus as in claim 9, wherein said first motor means comprises a cylinder, a piston in said cylinder and a piston rod having a rearward end attached to a forward end of said piston and a forward end connected to said second motor means cylinder for reciprocating said second motor means and thereby said plunger assembly and said sampler body.

11. Sampling apparatus as in claim 10, wherein said first motor means is rearward of said second motor means and said first motor means piston rod and said plunger means are axially aligned.

12. Sampling apparatus as in claim 1, wherein the fluid product is of a type that forms a dead layer of built up, deposited or stagnant product on inner walls of the process line, and said coupling means couples said sampler body to the process line in sealed relation to the process line for reciprocation of said sampler body by said motor means relative to said coupling means and the process line to move said sampler body forward end forward to a position in the flow stream inwardly of the dead layer of product and rearward to a position to the exterior of the flow stream.

13. Sampling apparatus as in claim 12 wherein said motor means comprises first and second motor means, said second motor means is coupled to said plunger means and said sampler body for reciprocating said plunger means in said sampler body bore relative to each of said sampler body, said coupling means and the process line, and said first motor means is coupled to said second motor means for reciprocating each of said second motor means, said plunger means and said sampler body relative to said coupling means and the process line.

14. Sampling apparatus as in claim 13, wherein said second motor means comprises pneumatic motor means having a cylinder coupled to said sampler body and a piston coupled to said plunger means, and said first motor means comprises pneumatic motor means having a cylinder coupled to said coupling means and a piston coupled to said second motor means cylinder.

15. Sampling apparatus as in claim 13, wherein said first motor means is operable to reciprocate forward all of said second motor means, said sampler and said plunger means to move said sampler body forward end from said first position to said second position, said second motor means is operative, when said sampler body forward end is in said second position, to reciprocate said plunger means between said sample obtaining and delivering positions, and said first motor means also is operable to reciprocate all of said second motor means, said sampler body and said plunger means rearward to move said sampler body forward end rearward from said second position to said first position.

16. Sampling apparatus for obtaining discrete samples of fluid product from a flow stream of product flowing through a process line, wherein the product is of a type that forms a dead layer of product on inner walls of the process line, comprising:
   a sampler body having a bore and a forward opening from said bore at a forward end of said sampler body;
   means for coupling said sampler body to the process line at an opening to the process line for reciprocation of said sampler body forward end within the process line;
   a sampler plunger received in said sampler body bore, said plunger having a fluid sample receiver intermediate forward and rearward ends thereof, and
   motor means for reciprocating said sampler body forward end forward from a first position that is to the exterior of the flow stream to a second position in the interior of the flow stream and then rearward from said second position to said first position, said motor means, when said sampler body forward end is in said second position, being operable to reciprocate said plunger in said bore forward, from a sample delivering position, to extend said plunger and said sample receiver from said forward bore opening and into the interior of the fluid stream to a sample obtaining position to obtain a sample of product in said sample receiver and then in a rearward direction from said sample obtaining position to said sample delivering position.

17. Sampling apparatus as in claim 16, including means in said sampler body bore at said sample delivering position for receiving the fluid sample from said sample receiver.

18. Sampling apparatus as in claim 16, including seal means on said plunger on opposite sides of said sample receiver for maintaining a fluid seal between said bore forward opening and said sample delivering position during operation of said fluid sampler.

19. Sampling apparatus as in claim 16, wherein said motor means comprises first and second motor means.

20. Sampling apparatus as in claim 19, wherein said first motor means reciprocates said sampler body between said first and second positions and said second motor means reciprocates said plunger between said sample obtaining and delivering positions.

21. Sampling apparatus as in claim 20, wherein said second motor means is coupled to said sampler body for reciprocation therewith and said first motor means is coupled to said second motor means to reciprocate said second motor means and said sampler body.

22. Sampling apparatus as in claim 21, wherein said second motor means comprises pneumatic motor means having a cylinder and a piston in said cylinder coupled to a rearward end of said plunger for reciprocating said plunger in said sampler body bore between said sample obtaining and delivering positions, and said first motor means comprises pneumatic motor means having a cylinder and a piston in said cylinder coupled to said second motor means cylinder for reciprocating said second motor means to reciprocate said sampler body between said first and second positions.

23. Sampling apparatus as in claim 22, wherein said first motor means includes a piston rod having a rearward end coupled to said first motor means piston and a forward end coupled to said second motor means cylinder.

24. Sampling apparatus as in claim 23, wherein said first motor means is rearward from said second motor means and said first motor means piston rod and said plunger are coaxial.

25. A method of sampling a fluid product in a flow stream in a process line, comprising the steps of:

providing a sampler body having a longitudinal bore and a forward opening from the bore at a forward end of the sampler body;

positioning a plunger, having a sample obtaining recess intermediate forward and rearward ends thereof, in the bore;

extending the forward end of the sampler body from a first position to the exterior of the flow stream through an opening in the process line to a second position in the interior of the flow stream;

while the sampler body forward end is at the second position, reciprocating the plunger to extend the plunger forward through the sampler body bore from a sample delivering position to a sample obtaining position where the plunger recess is projected out of the forward opening from the sampler body bore and into the flow stream to obtain in the recess a sample of the product, and to then retract the plunger rearward through the sampler body bore from the sample obtaining position to the sample delivering position in the bore;

collecting the sample from the recess at the sample delivering position;

sequentially repeating said plunger reciprocating step, and periodically retracting the sampler body forward end from the second position to the first position.

26. A method as in claim 25, wherein the product is of a type that forms a dead layer of product on inner walls of the process line and said step of extending the sampler body forward end to the second position extends the forward end through and inwardly beyond the dead layer of product.

* * * * *